United States Patent [19]

Chiba

[11] Patent Number: 4,857,541

[45] Date of Patent: Aug. 15, 1989

[54] SUBSTITUTED BENZIMIDAZOLE FUNGICIDE

[75] Inventor: Mikio Chiba, St. Catharines, Canada

[73] Assignee: Canadian Patents and Development Limited/Societe Canadienne Des Brevets et D'Exploitation Limitee, Ottawa, Canada

[21] Appl. No.: 894,029

[22] Filed: Aug. 7, 1986

[51] Int. Cl.$^4$ ............................................. A01N 43/40
[52] U.S. Cl. .................................................... 514/388
[58] Field of Search .......................... 514/388; 548/306

[56] References Cited

U.S. PATENT DOCUMENTS 3,541,213 11/1970 Klopping ............................. 514/388
3,631,176 12/1971 Klopping ............................. 548/306

FOREIGN PATENT DOCUMENTS 820317 8/1969 Canada .

OTHER PUBLICATIONS

*Localization of the Site of Action of a Fungitoxic Benomyl Derative*, G. P. Clemons & H. D. Sisler, Pesticide Biochemistry and Physiology 1, 32, 43, 1971.

Primary Examiner—Allen J. Robinson
Attorney, Agent, or Firm—Banner, Birch, McKie & Beckett

[57] ABSTRACT

A fungicide which is particularly effective against benomyl resistant fungi is selected from the group of fungicides represented by the formula:

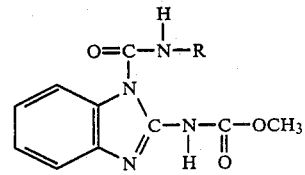

wherein R is $C_nH_{2n+1}$ and n is 1, 2, 3 or 6 or R is phenyl. The method comprises applying as a suspension an effective amount of the one or more fungicides selected from the formula to benomyl resistant fungi, such as benomyl resistant isolates of *Botrytis cinerea*.

8 Claims, 2 Drawing Sheets

SUBSTITUTED BENZIMIDAZOLE FUNGICIDE

FIELD OF THE INVENTION

This invention relates to fungicides which are particularly effective against benomyl resistant fungi.

BACKGROUND OF THE INVENTION

Benomyl is a widely used fungicide which has been effective worldwide against many diseases of commercially important crops. However, the repeated use of benomyl has resulted in the selection of benomyl resistant fungal isolates against which benomyl has significantly reduced activity, thereby necessitating the use of alternative and often less effective fungicides.

There has been considerable research in the field of fungicides in an attempt to locate a fungicide which is not only effective against the fungal isolates which are benomyl resistant, but also effective against fungi which are sensitive to benomyl. As reported by G. P. Clemons and H. G. Sisler in Pesticide Biochemistry and Physiology, Volume 1, pp. 32-43, 1970, it was believed that benomyl degrades to methyl 2-benzimidazolecarbamate which was thought to be the effective ingredient of the fungicide. As a result, most research has been directed at locating other types of fungicides which would be effective against the benomyl resistant fungal isolates. However, this research has not led to any significant fungicide which is useful in this area.

Benomyl has the chemical formula, methyl 1-(butylcarbamoyl)-2-benzimidazolecarbamateis as disclosed in Canadian Pat. No. 820,317. The fungicidal properties of benomyl and other types of methyl-2-benzimidazolecarbamates are disclosed as being useful as fungicides. However, since it was generally understood that benomyl degraded rapidly to methyl-2-benzimidazolecarbamate (BMC), there have been no investigations to determine if any of the other related compounds disclosed in this patent specification would have any effect on benomyl resistant fungal isolates.

SUMMARY OF THE INVENTION

According to an aspect of this invention, a method of using a fungicide selected from the group consisting of compounds represented by the formula:

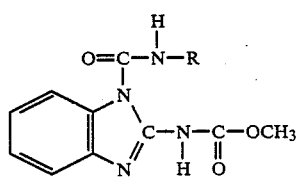

(I)

wherein R is $C_nH_{2n+1}$ and n is 1, 2, 3 or 6, or R is phenyl, is provided. The method comprises applying in a suitable carrier an effective amount of one or more of the fungicides selected from the group of fungi which are resistant to a fungicide, benomyl, of above Formula I, wherein R is $C_4H_9$.

According to another aspect of the invention, a selected fungicide of the Formula is applied to crops having the benomyl resistant fungi.

According to another aspect of the invention, the selected one or more fungicides are particularly effective against benomyl resistant isolates of *Botrytis cinerea*.

BRIEF DESCRIPTION OF THE DRAWINGS

Preferred embodiments of the invention are shown in the drawings, wherein.

DETAILED DESCRIPTION OF THE INVENTION

Figure 1:
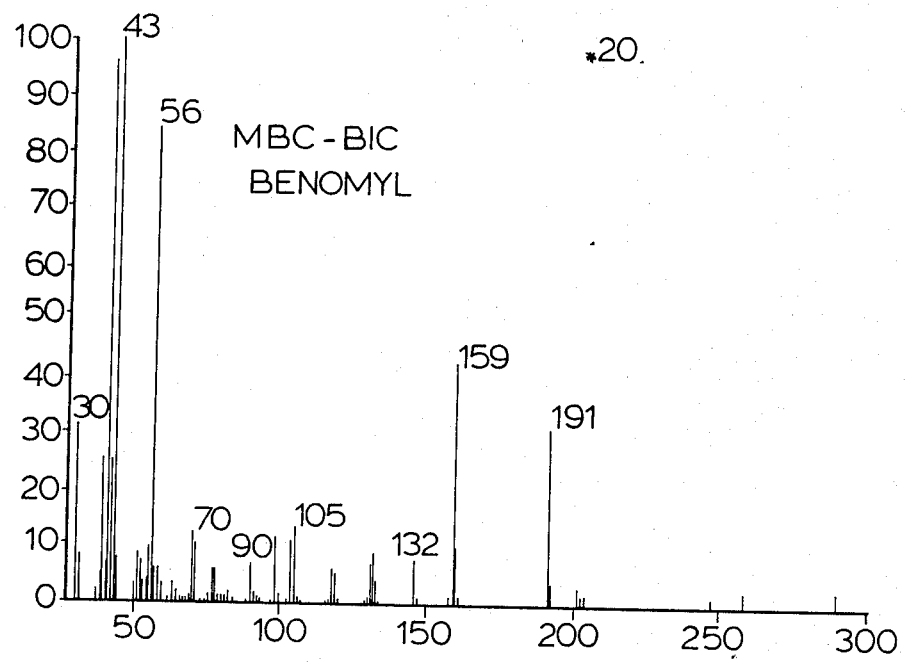
FIGS. 1, 2, 3 and 4 illustrate mass spectrometry analysis of various benzimidazolecarbamate fungicides.

Apple crops, grape vine crops and many other types of crops are affected by various types of fungi. In apple and grape crops, the *Botrytis cinerea* is a particularly destructive type of fungus. Hence for many years fungus growers have been using benomyl which is methyl 1-(butylcarbamoyl)-2-benzimidazolecarbamate to control the fungi during the crop growing season. However, users of benomyl have been experiencing serious problems, because many fungi, including isolates of *Botrytis cinerea* have developed benomyl resistance after several years of continuous use and sometimes even within a year after several applications. Hence users have had to use alternative fungicides of lesser efficacy (captan and iprodione, for example) with a risk of inducing another type of resistance (iprodione, for example). An additional problem with the use of benomyl is that many fungi resistant to this particular fungicide are also resistant to other benzimidazole compounds which is a phenomenon known as cross-resistance.

Fungicides have been developed which are effective against fungi which are benomyl resistant. However, these fungicides have proven to be less effective against benomyl sensitive fungi. If the current rate of loss of fungicides, because fungicide resistance continues, there will be a serious shortage of effective fungicides currently available on the market. This has led to continued pressure on research to develop new effective fungicides. As noted, most research has been directed at developing fungicides which are not related to benzimidazoles, because it was thought that benomyl and other benzimidazoles degraded to MBC (methyl-2-benzimidazolecarbamate), which is the major source of inducing resistance. Hence any similar benzimidazolecarbamates will have little if any effect on the benomyl resistant strains of fungi. Contrary to this well understood theory, it has been discovered surprisingly that fungicides closely related to benomyl are effective against benomyl resistant strains of fungi. Accordingly, this invention provides a method of using fungicides selected from the group consisting of compounds represented by the formula

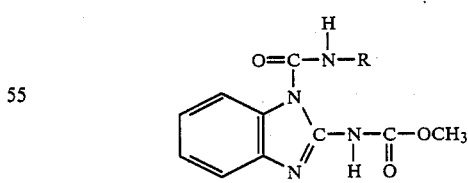

The particular fungicides of the formula are those where R is $C_nH_{2n+1}$. n may be 1, 2, 3 or 6 or alternatively R is phenyl. These compounds are specifically named as follows:

methyl-1-(methylcarbamoyl)-2-benzimidazolecarbamate methyl-1-(ethylcarbamoyl)-2-benzimidazolecarbamate methyl-1-(propylcarbamoyl)-2-benzimidazolecarbamate methyl-1-(hexylcarbamoyl)-2-benzimidazolecarbamate
methyl-1-(phenylcarbamoyl)-2-benzimidazolecarbamate.

Benomyl, which is is methyl 1-(butylcarbamoyl)-2-benzimidazolecarbamate, is a homologue of the above compounds of the formula wherein R is $C_4H_9$ (butyl). The fungicides, as used in accordance with this invention, may be synthesized by the reaction between methyl-2-benzimidazolecarbamate and the methyl, ethyl, propyl, hexyl and phenyl isocyanates to yield the desired compounds. Such synthesis is exemplified in Canadian Pat. No. 820,317. It is depicted as follows

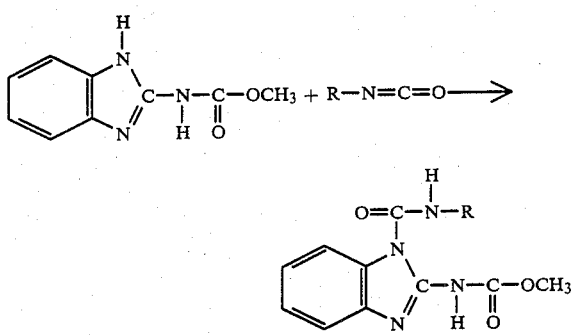

wherein R is defined as above.

Figure 2:
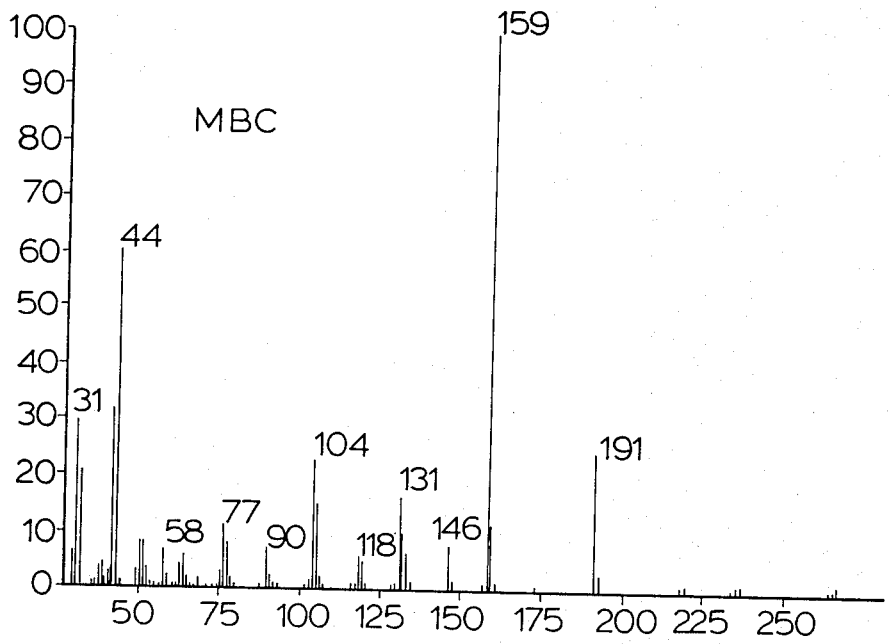
Figure 3:
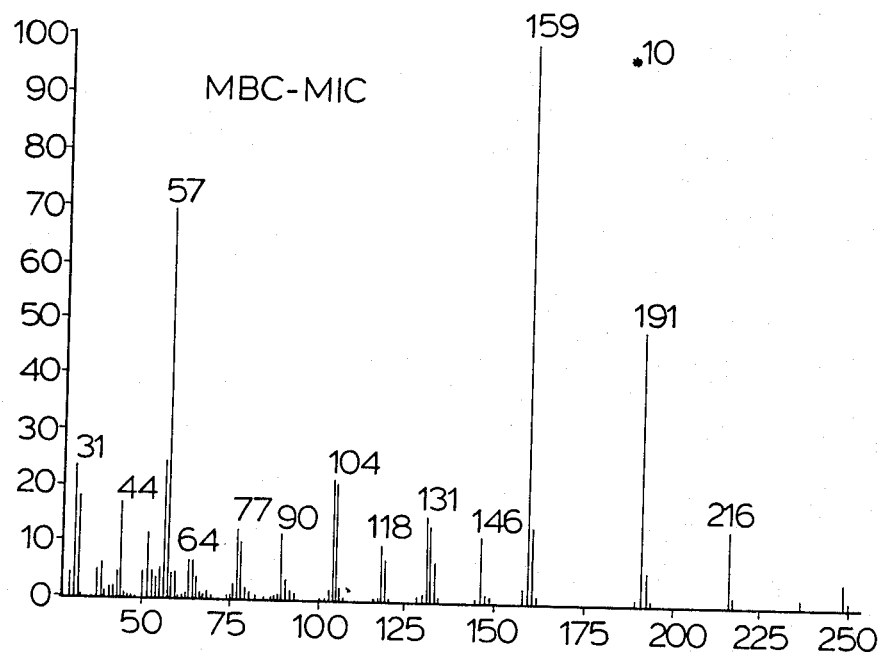
Figure 4:
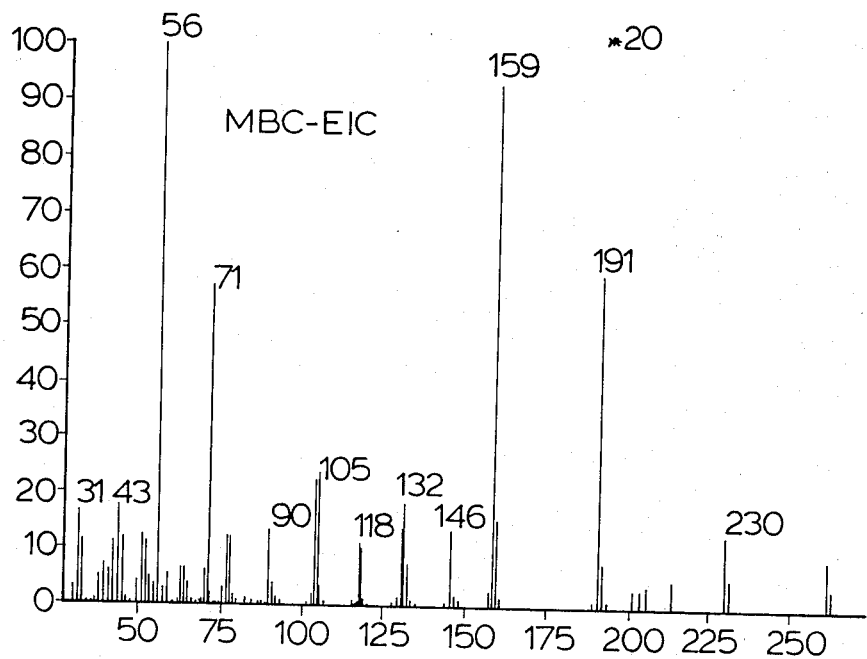

FIGS. 1 through 4 show the results of mass spectrometry measurements carried out to confirm that the known compounds of benomyl and methyl-2-benzimidazolecarbamate are distinctly different from two of the fungicides used in accordance with this invention which are the methyl 1-(methylcarbamoyl)-2-benzimidazolecarbamate and the methyl 1-(ethylcarbamoyl)-2-benzimidazolecarbamate.

It has been unexpectedly discovered that the application of these benomyl homologues to benomyl resistant isolates of various fungi are very effective against such fungi, as well as the benolyl sensitive fungi. For example, the benomyl resistant isolate of Botrytis cinerea is killed by these benomyl homologues at considerably reduced concentrations than with benomyl. This particular fungal isolate is very common on grapes, apples, and strawberries, and vegetables and ornamentals, so that the discovery of particularly useful fungicide has significant impact on the commercial viabilities of these crops. It is appreciated that in using the fungicides, according to this invention, they may be mixed with suitable additives to facilitate their application to crops, such as the same compounding used in the method of administering benomyl to various crops. Effective concentrations of the active compound in a carrier is normally in the range of 250-2000 ppm. The carrier may be a medium in which the fungicide is suspended, such as water. When such use suspensions are sprayed on crops, the distribution of the active compound should normally be in the range of 0.5 to 4 kg active fungicide per hectare of crop, the concentration varying depending upon the crop to which the fungicide is applied, for example, apples, grapes and strawberries, and vegetables and ornamentals.

The following Examples exemplify various aspects of the invention which are in no way intended to be limiting to the scope of the appended claims.

EXAMPLE 1

Method of Synthesis

To 1 g of MBC (methyl-2-benzimidazolecarbamate), 20 ml of $CHCl_3$ was added. After mixing well, 10 ml of methyl isocyanate was added. The mixture was stirred to dissolve the MBC completely. After 10 min of additional stirring, 150 ml of hexane was added. The formed precipitate of methyl 1-(methylcarbamoyl)-2-benzimidazolecarbamate was filtered through a sintered glass filter. The precipitate was washed with isocyanate containing hexane and vacuum dried at 20° C. The yield was 76-87%.

This method may be used to prepare also the ethyl, propyl, hexyl and phenyl carbamoyl derivatives. When making the hexyl carbamoyl derivative, preconcentration of the $CHCl_3$ solution before adding hexane is desirable.

EXAMPLE 2

Toxicity of Benzimidazole Compounds to Botrytis cinerea

Two monoconidial isolates of Botrytis cinerea, one sensitive (S) and the other resistant (R) to benomyl had been isolated from grapes in 1984 and had been maintained on potato dextrose agar (PDA), non-amended and amended with benomyl (1 ug/mL, 3.4 $\mu M$) for the S and R isolates respectively. Fresh cultures were grown on PDA in the dark for 3 days and then in fluorescent light (300 uE/m$^2$/sec) with a 16 hr daily photoperiod for 7 to 10 days to induce sporulation. The spore suspension was prepared by shaking a culture in sterile distilled water, followed by filtration and adjustment of the spore suspension to the required concentration with distilled water.

Fungitoxicity test

The spore suspension was combined with salts and dextrose to stimulate spore germination, and combined with Tween 20 and fungicide to give the following final concentrations:

| | |
|---|---|
| Spores | 3 × 10$^4$ conidia/mL |
| Dextrose | 10 g/L (1%) |
| K citrate, Na citrate | 0.01 g/L, 0.01 g/L |
| Tween 20 | 0.05 g/L |
| Fungicide | check, 0.032-564 $\mu M$ (19 levels) |

The fungicides employed are as follows:

| | |
|---|---|
| MBC | methyl-2-benzimidazolecarbamate |
| MBC-MIC | methyl 1-(methylcarbamoyl)-2-benzimidazolecarbamate |
| MBC-EIC | methyl 1-(ethylcarbamoyl)-2-benzimidazolecarbamate |
| MBC-PIC | methyl 1-(propylcarbamoyl)-2-benzimidazolecarbamate |
| MBC-BIC (benomyl) | methyl 1-(butylcarbamoyl)-2-benzimidazolecarbamate |
| MBC-HIC | methyl 1-(hexylcarbamoyl)-2-benzimidazolecarbamate |

The combined inoculum-fungicide-stimulant suspensions were dispensed as 30 uL drops, with 4 replicate drops spotted on the inner lid surface of an inverted 100 mm diameter polystyrene petri dish. The other part of the dish covered the drops to prevent evaporation. The germination test was conducted at 21° C. and was terminated after 20 hr with a 30 uL drop of Na azide (2 g/L) in 10% aqueous glycerol. For each of the four replicate drops, 50 conidia were examined and considered "germinated" if the length of the germ tube exceeded the length of the spore, and the individual germ tube lengths of ten germinated spores were measured. The experiment with each of the six fungicide compositions was repeated and the eight replicate observations were averaged and the percentage inhibition values were calculated and plotted on probability-5 cycle log concentration graph paper. Values showing a linear distribution close to 50% inhibition ($EC_{50}$) were analyzed using a Probit-log concentration program which yielded the $EC_{50}$ value with its 95% confidence limits and the slope of the response curve with its 95% confidence limits. The results are shown in following Tables I and II.

Protection of Wounded Apples

Cold-stored McIntosh apples were surface-sterilized with 1.5% available chlorine solution, rinsed, dried and 18 apples were arranged on lids in a paper-lined wooden box 30 cm×24 cm i.d. constituting one treatment unit. Each apple was wounded once with an ethanol-surface-sterilized nail, 4 mm diameter, to a depth of 4 mm, and to each freshly made wound was added a 30 uL drop of freshly prepared spore suspension with $10^5$ conidia/mL. Two hours after inoculation, when the inoculum drop had been absorbed or evaporated, a 30 uL drop of fungicide suspension with Tween 20 and germination stimulants, as used in the spore germination study, was added to particular treatments as shown in the following Table III. The percentage of fruits with lesions was determined after 7 days incubation at 21° C. at high humidity (95%).

The percentage inhibition of infection in relation to selected concentrations of MBC, MBC-EIC and MBC-BIC, for both the S and R isolates were examined by a Probit-log concentration program to calculate the $EC_{50}$ and $EC_{95}$ values and their 95% confidence limits.

TABLE I

Concentrations of Benzimidazole Compounds Giving 50% Inhibition ($EC_{50}$) of Germ Tube Length of *Botrytis cinerea* Spores, Sensitive (S) and Resistant (R) to Benomyl, and the Relative Toxicity or Resistance Factor (Rf).

| Compound | $EC_{50}$ (μM), germ tube length | | |
|---|---|---|---|
| | S | R | Rf[1] |
| MBC | 0.14 a[2] | >564 | >4029 |
| MBC-MIC | 0.23 b | 0.97 cd | 4 |
| MBC-EIC | 0.20 ab | 0.60 c | 3 |
| MBC-PIC | 0.18 ab | 2.1 e | 12 |
| MBC-BIC (benomyl) | 0.21 ab | 13.2 f | 63 |
| MBC-HIC | 0.72 c | 6.2 f | 9 |

[1] Rf, relative toxicity or resistance factor = $EC_{50}$ R/$EC_{50}$S
[2] Values follows by different letters differ significantly (P = 0.05)

TABLE II

Concentrations of Benzimidazole Compounds Giving 50% Inhibition ($EC_{50}$) of Germination of *Botrytis cinerea* Spores, Sensitive (S) and Resistant (R) to Benomyl, and the Relative Toxicity of Resistance Factor (Rf).

| Compound | $EC_{50}$ (μM), germination | | |
|---|---|---|---|
| | S | R | Rf[1] |
| MBC | 316 d[2] | >564 | >1.8 |
| MBC-MIC | 18 b | 17 b | 0.92 |
| MBC-EIC | 115 cd | 7 a | 0.06 |
| MBC-PIC | 376 d | 55 c | 0.15 |
| MBC-BIC (benomyl) | 161 d | >317 | >2.0 |
| MBC-HIC | 138 d | >564 | >4.1 |

[1] Rf, relative toxicity or resistance factor = $EC_{50}$ R/$EC_{50}$S
[2] Values follows by different letters differ significantly (P = 0.05)

TABLE III

Inhibition of Wound Infections of Apple by Benomyl Sensitive (S) and Benomyl Resistant (R) *Botrytis cinerea* by MBC, MBC-EIC and MBC-BIC (Benomyl).

| Homologue Concentration (μM) | MBC | | MBC-EIC | | MBC-BIC | |
|---|---|---|---|---|---|---|
| | S | R | S | R | S | R |
| 3170 | —[1] | 0[2] | — | — | — | 0 |
| 1787 | — | 0 | — | — | — | 0 |
| 1000 | — | 0 | — | 100 | — | 0 |
| 564 | — | 0 | — | 89 | — | 0 |
| 317 | — | — | 100 | 67 | — | — |
| 178 | 100 | — | 94 | 39 | 100 | — |
| 100 | 100 | — | 89 | 6 | 100 | — |
| 56 | 89 | — | 67 | 11 | 83 | — |
| 32 | 61 | — | 50 | — | 11 | — |
| 18 | 17 | — | 11 | — | 11 | — |
| 0 (check) | 0[2] | 0 | 0 | 0 | 0 | 0 |

[1] Not Tested
[2] 100% infection

Using inhibition of germ tube length as a measure of relative fungitoxicity, MBC-MIC, MBC-EIC and MBC-PIC were as effective as MBC-BIC (benomyl) against benomyl sensitive (S) *Botrytis cinerea*. Against benomyl resistant (R) *B. cinerea*, these three compounds were markedly more effective than MBC-BIC and MBC.

Benzimidazole compounds generally show less effect on spore germination than on the subsequent growth of the germ tube, and this was confirmed by high $EC_{50}$ values. In the spore germination study, MBC-MIC was significantly more inhibitory than MBC-BIC and showed similar activity towards both the S and R isolates. In contrast, negative cross resistance was shown by MBC-EIC and MBC-PIC, with the R isolate being more sensitive than the S isolate. However, negative cross resistance was not shown in the germ tube inhibition study, where low Rf values of 3 and 11 were show, respectively.

In the wounded apple study, MBC-EIC provided protection at 317 uM comparable to that of MBC-BIC and MBC at 100 uM, against the S isolate. Against the R isolate, MBC-EIC gave complete protection at 1000 uM in contrast to the total ineffectiveness of MBC-BIC and MBC at 3170 uM.

Four alkyl isocyanate homologues of benomyl were compared for their toxicity to benomyl sensitive (S) and benomyl resistant (R) isolates of *Botrytis cinerea* using a laboratory spore germination test. The methyl and ethyl homologues (MBC-MIC and MBC-EIC respectively) were as effective against the S isolate and more effective against the R isolate than benomyl (MBC-BIC), using 50% inhibition ($EC_{50}$) of germination and germ tube length as criteria. For the protection of wounded apples, MBC-EIC was much more effective against the R isolate than benomyl and was only slightly less effective than benomyl against the S isolate.

The effectiveness of the methyl 1-(hexylcarbamoyl)-2-benzimidazolecarbamate also predicts that the methyl 1-(phenylcarbamoyl)-2-benzimidazolecarbamate is equally effective as a fungicide against benomyl sensitive and benomyl resistant *Botrytis cinerea*. From the above results, the MBC-EIC and the MBC-MIC appear to be the most effective fungicides for use against fungal isolates which are resistant to benomyl.

Although preferred embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. A method of using a fungicide against fungi which are resistant to benomyl said fungicide being selected from the group consisting of compounds represented by the formula:

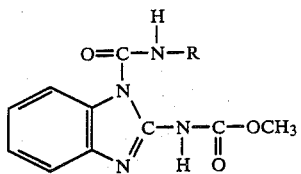

wherein R is $C_nH_{2n+1}$ and n is 1, 2, 3 or 6 or R is phenyl, said method comprising applying in a carrier a fungicidally effective amount of one or more fungicides selected from said group to fungi which are resistant to the fungicide, benomyl.

2. A method of claim 1, wherein a single said fungicide selected from said group is methyl 1-(methylcarbamoyl)-2-benzimidazolecarbamate.

3. A method of claim 1, wherein a single said fungicide selected from said group is methyl 1-(ethylcarbamoyl)-2-benzimidazolecarbamate.

4. A method of claim 1, wherein a single said fungicide selected from said group is methyl 1-(propylcarbamoyl)-2-benzimidazolecarbamate.

5. A method of claim 1, wherein a single said fungicide selected from said group is methyl 1-(hexylcarbamoyl)-2-benzimidazolecarbamate.

6. A method of claim 1, wherein a single said fungicide selected from said group is methyl 1-(phenylcarbamoyl)-2-benzimidazolecarbamate.

7. A method of claim 1, wherein said fungicidally effective amount of said one or more selected fungicides is approximately 250–2000 ppm in said carrier.

8. A method of claim 1, wherein said fungicidally effective amount of said one or more selected fungicides in said carrier is sufficient to apply approximately 0.5 to 4 kg of said one or more selected fungicides per hectare of crop having said benomyl resistant fungi.

* * * * *